United States Patent [19]

Indech

[11] 4,343,301
[45] Aug. 10, 1982

[54] SUBCUTANEOUS NEURAL STIMULATION OR LOCAL TISSUE DESTRUCTION

[76] Inventor: Robert Indech, 46 Roger Williams Green, Providence, R.I. 02904

[21] Appl. No.: 81,884

[22] Filed: Oct. 4, 1979

[51] Int. Cl.³ .................... A61H 23/00; A61H 39/00
[52] U.S. Cl. .................................................. 128/24 A
[58] Field of Search ............ 128/420 A, 24 A, 24 R, 128/663, 660, 32, 33, 24 A

[56] References Cited

U.S. PATENT DOCUMENTS

| | | | |
|---|---|---|---|
| 2,968,302 | 1/1961 | Fry et al. | 128/24 A |
| 3,499,437 | 3/1970 | Balamuth | 128/24 A |
| 3,987,673 | 10/1976 | Hansen | 128/663 |
| 4,023,574 | 5/1977 | Nemec | 128/420 A |
| 4,105,024 | 8/1978 | Raffel | 128/33 |
| 4,153,061 | 5/1979 | Nemec | 128/420 A |

FOREIGN PATENT DOCUMENTS

| | | | |
|---|---|---|---|
| 2801796 | 7/1979 | Fed. Rep. of Germany | 128/804 |
| 624626 | 9/1978 | U.S.S.R. | 128/24 A |
| 628914 | 10/1978 | U.S.S.R. | 128/24 A |

OTHER PUBLICATIONS

Fry et al.; The Use of Ultrasound in Neurosurgery; 3rd International Conference on Medical Electronics, London, 1960.

*Primary Examiner*—Stephen C. Pellegrino
*Assistant Examiner*—John C. Hanley

[57] ABSTRACT

A method of generating a high energy density at any point in the body, noninvasively, by two high frequency sonic beams creating a low frequency beating pattern at their intersection locus. One method provides for two transducers at different angular positions. Each transducer produces a beam pattern of high frequency. One transducer produces a high frequency which is higher by a predetermined quantity than the other. At their point of intersection, the sonic oscillations add and subtract, producing a low frequency beat equal to the predetermined quantity. This high energy low frequency beat can be used to stimulate neural points in the skull or other parts of the body or for tissue destruction. In a related method, the high frequency beams are set in axial alignment so that the frequency generating output is fixed between the transducers. A master modulator can then be used to electronically vary the position of the intersecting locus along the axial line connecting the transducers.

7 Claims, 2 Drawing Figures

SUBCUTANEOUS NEURAL STIMULATION OR LOCAL TISSUE DESTRUCTION

BACKGROUND OF THE INVENTION

It has been determined that high frequency sound waves can be used to affect human tissue and stimulate nerves. Further, a high energy low frequency wave produces a more positive marked effect by periodic pressure changes, particle acceleration, etc. If it is possible to pinpoint and aim such a high energy low frequency wave to a single point in the body, many advantages would flow. Such a method will allow for a form of noninvasive neurosurgery, or stimulation of the spinal cord for pain elimination or message transmission noninvasively. It can stimulate regional centres of the brain for artificial vision, artificial hearing, or pleasure responses. It can also be used to destroy tumors, clots, etc. through local heating.

SUMMARY OF THE INVENTION

The present invention provides a method and means for producing the desired low frequency high energy beam at a point within the body without invasion of the body. One method provides for two transducers at different angular points outside of the body. Each produces a high frequency beam, one being slightly higher than the other by a predetermined quantity. At their point of intersection, the sonic oscillations add and subtract producing a low frequency high energy beat equal to the predetermined quantity. In a related method, the high frequencies are set in axial alignment so that the frequency generating output is fixed between the transducers. A modulator can then be used to electronically vary the timing so that the position of the intersecting locus along the axial line can be varied.

DESCRIPTION OF THE INVENTION

Figure 1:
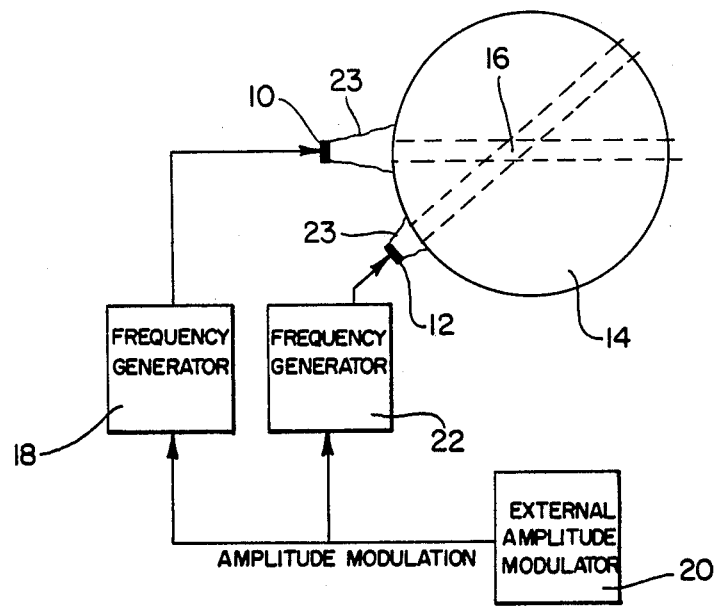
FIG. 1 is a diagrammatic view of a single locus, dual cell device of the present invention.

The basic method of applying a high energy low frequency beat to a predetermined point within the body is illustrated in FIG. 1. A pair of transducers 10 and 12 are positioned about a human skull 14 to produce high frequency beams which intersect at the point 16 within the skull 14.

The transducer 10 is actuated by a frequency generator 18 which is in turn controlled by the amplitude modulator 20. The transducer 12 is actuated by a frequency generator 22 also controlled through the amplitude modulator 20. The transducer 10 produces a high frequency beam f1, which, for example, can be in the range of 1000 Hertz or more. The transducer 12 provides a high frequency beam $f1 + \Delta f$ in which the value of $\Delta f$ may equal 100 Hertz or less.

With the above arrangement and values, it will be found that a high energy low frequency beat, equivalent to the value of $\Delta f$, is produced at the point of intersection 16, the high frequencies f1 continuing in diverging lines through the skull. In effect, the sonic oscillations are of themselves of sufficiently high frequency to pass through without affecting the body while producing the low frequency high energy beat at the point of intersection 16. The transducer output may be mechanically coupled to the scalp by any conventional gel coupling agent 23.

The advantages of this method are many. It will allow a form of noninvasive surgery. It will stimulate the spinal cord for pain elimination or message transmission noninvasively. It can stimulate regional centres of the brain to produce artificial vision or hearing or for pleasure responses. It can be used to destroy tumors, blood clots, etc. through local heating.

Figure 2:
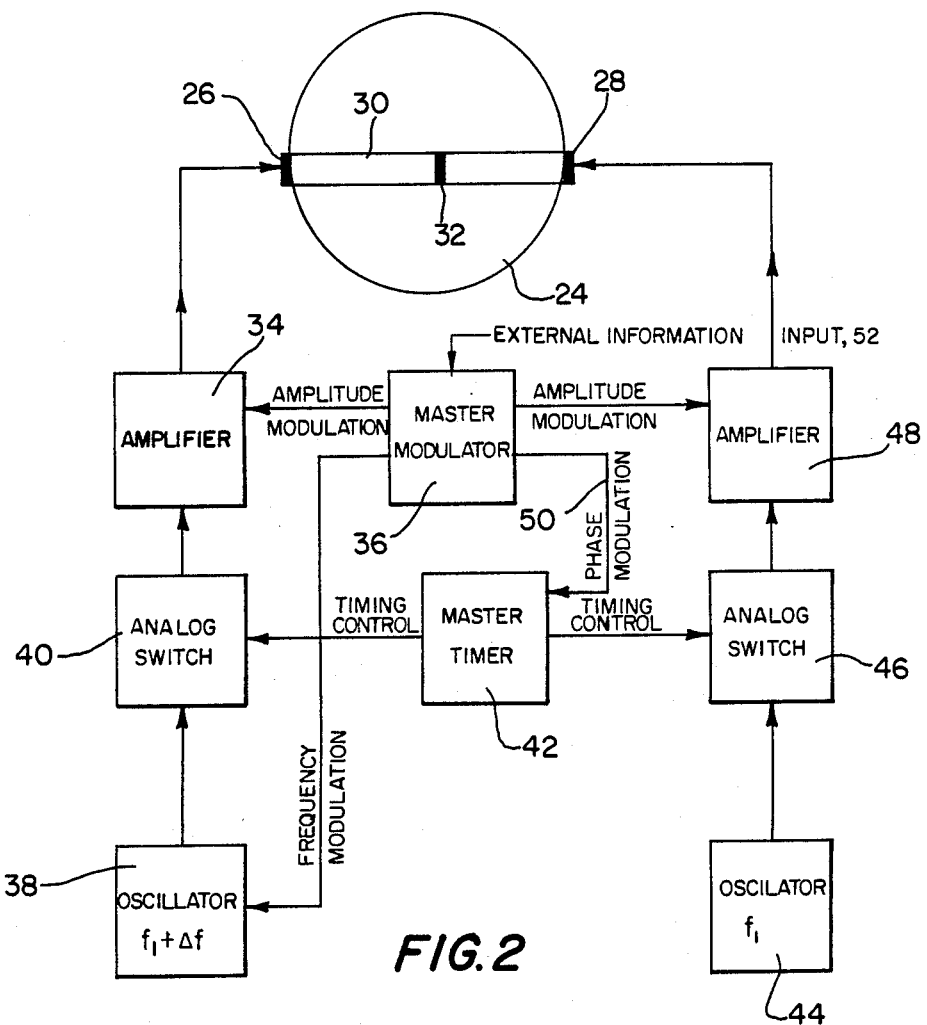
FIG. 2 is a diagrammatic view of a multi-locus, dual cell device.

The method used in FIG. 1 pinpoints the locus at a predetermined point of intersection. FIG. 2 illustrates a method of varying the locus within the body. In this form, the transducers are positioned on opposite sides of the skull 24. The transducers 26 and 28 face each other in axial alignment to produce high frequency beams 30.

Where the transducer 26 produces a high frequency wave $f1 + \Delta f$, and the transducer 28 produces a high frequency wave f1, a high energy low frequency beat equal to $\Delta f$ is produced along the beams 30 at a time-space intersection 32, as well as a high frequency beat $f1 + f1 + \Delta f$. The position of the point 32 along the axis of the beam 30 can be varied by varying the timing of the wave lengths of the transducers. This allows the low frequency beat to be moved along the beam 30.

The electronic connections are simple. The transducer 26 is actuated through an amplifier 34 and amplitude modulator 36. The modulator 36 is connected to an oscillator 38 for the $f1 + \Delta f$ frequency which passes through an analog switch 40 to the amplifier 34. A master timer 42 controls the switch 40.

At the transducer 28, the oscillator 44 is connected to the analog switch 46 which is also controlled by the master timer 42. The analog switch 46 connects to the amplifier 48 controlled by the modulator 36 and connected to the transducer 28. Thus, by varying the master timer, the locus of the low frequency beat can be varied along the axis of the beam 30. Further, the locus of the low frequency beat may be varied to transfer information to the brain by external information input 52 to the master modulator 36.

In both methods, a pair of high frequency sound waves are caused to intersect at the point of operation to produce a low frequency high energy beat. In both cases this is accomplished by allowing the high frequencies to internally heterodyne and leave the low frequency which has been added to one of the waves. In one case the phenomenon is directed to a single fixed point. In the second method, the point of operation can be moved along a fixed line.

Thus, the present method allows for the internal imposition of a low frequency high energy beat without the invasion of the corpus. The technique is simple and easy and should result in a great deal of accuracy regarding the positioning of the beat. This method can also be applied to any device in which it is desired to produce a low frequency high energy beat or heat at a predetermined point in the device without invasion. Other advantages of the present invention will be readily apparent to a person skilled in the art.

I claim:

1. A method of noninvasively stimulating a neuron within a body via a mechanical resonance produced by a low frequency sonic beat comprising the steps of positioning a pair of transducers on the body so that the sonic waves emanating therefrom will intersect, sending a high frequency sonic wave from one transducer, sending a high frequency sonic wave from the other transducer, one of said sonic waves having a slightly higher frequency than the other, whereby a low frequency beat is produced at the intersection of said waves equal to the difference in frequency between said waves, whereby said low frequency beat is sufficient in amplitude to produce an action potential at a neuron situated at said intersection point, and directing said intersection to a predetermined point within the body.

2. The method as in claim 1, wherein the frequency of one of said sonic waves is 1000 Hertz or more and the frequency of the second of said waves is the same as the first plus 100 Hertz or less.

3. The method as in claim 1, wherein said transducers are positioned to direct their sonic waves at an angle of less than 180° to intersect within the body.

4. The method as in claim 3, wherein the frequency of one of said sonic waves is 1000 Hertz or more and the frequency of the second of said waves is the same as the first plus 100 Hertz or less.

5. The method as in claim 1, wherein the point of positioning of the low frequency beat may be varied within the body.

6. The method as in claim 5, wherein said transducers are in opposed position to produce sonic beams along an axial line between them, the position of said low frequency beat being variable along said axial line.

7. The method as in claim 6, wherein the frequency of one of said sonic waves is 1000 Hertz or more and the frequency of the second of said waves is the same as the first plus 100 Hertz or less.

* * * * *